United States Patent
Termanini et al.

(10) Patent No.: US 11,020,242 B2
(45) Date of Patent: Jun. 1, 2021

(54) TOOL AND STATUS FOR SEPARATING A FEMORAL CUP FROM AN ACETABULAR BALL IN AN IMPLANTED HIP PROSTHESIS

(71) Applicant: HIP INNOVATION TECHNOLOGY, LLC., Boca Raton, FL (US)

(72) Inventors: Zafer Termanini, Port Saint Lucie, FL (US); Brian Vanhiel, Smyrna, GA (US)

(73) Assignee: HIP INNOVATION TECHNOLOGY, LLC., Boca Raton, FL (US)

( * ) Notice: Subject to any disclaimer, the term of this patent is extended or adjusted under 35 U.S.C. 154(b) by 0 days.

(21) Appl. No.: 15/742,192

(22) PCT Filed: Jul. 15, 2016

(86) PCT No.: PCT/US2016/042424
§ 371 (c)(1),
(2) Date: Jan. 5, 2018

(87) PCT Pub. No.: WO2017/019325
PCT Pub. Date: Feb. 2, 2017

(65) Prior Publication Data
US 2018/0193168 A1 Jul. 12, 2018

Related U.S. Application Data

(60) Provisional application No. 62/197,188, filed on Jul. 27, 2015.

(51) Int. Cl.
*A61F 2/46* (2006.01)
*A61F 2/32* (2006.01)
(Continued)

(52) U.S. Cl.
CPC .............. *A61F 2/4637* (2013.01); *A61F 2/32* (2013.01); *A61F 2/4607* (2013.01);
(Continued)

(58) Field of Classification Search
CPC ...... A61F 2002/4641; A61F 2002/4619; A61F 2/4637; A61F 2/4607; A61F 2/4609
See application file for complete search history.

(56) References Cited

U.S. PATENT DOCUMENTS 3,801,989 A * 4/1974 McKee ..................... A61F 2/32
623/22.12
4,457,306 A 7/1984 Borzone
(Continued)

FOREIGN PATENT DOCUMENTS

CN 102905649 A 1/2013
JP 2013521864 A1 6/2013

OTHER PUBLICATIONS

International Search Report for corresponding application PCT/US2016/042424 dated Oct. 4, 2016.
(Continued)

*Primary Examiner* — Amy R Sipp
(74) *Attorney, Agent, or Firm* — Norris McLaughlin PA

(57) ABSTRACT

Surgical tools which are used to separate from one another a femoral cup and an acetabular ball in an implanted hip replacement prosthesis. At its distal end, elements of the surgical tool engage the femoral cup and the acetabular cup. When proximal handles of the tool are squeezed toward one another, the engagement elements move away from one another. Thus, a surgeon is able to separate the femoral cup and the accetabular ball from one another without pulling the acetabular cup away from the acetabulum or the femoral cup and/or femoral implant away from the femur, thereby accomplishing the separation without disrupting any bone ingrowth.

13 Claims, 11 Drawing Sheets

(51) Int. Cl.
*A61F 2/30* (2006.01)
*A61F 2/34* (2006.01)
*A61F 2/36* (2006.01)

(52) U.S. Cl.
CPC .......... *A61F 2/4609* (2013.01); *A61F 2/4603* (2013.01); *A61F 2002/30538* (2013.01); *A61F 2002/3483* (2013.01); *A61F 2002/3615* (2013.01); *A61F 2002/4622* (2013.01); *A61F 2002/4641* (2013.01)

(56) References Cited

U.S. PATENT DOCUMENTS

| | | | | |
|---|---|---|---|---|
| 5,514,136 | A | * | 5/1996 | Richelsoph ........... A61F 2/4607 606/86 R |
| 5,735,857 | A | * | 4/1998 | Lane ................. A61B 17/8872 606/207 |
| 6,322,564 | B1 | | 11/2001 | Surma |
| 7,097,647 | B2 | | 8/2006 | Segler |
| 7,608,112 | B1 | | 10/2009 | Kuczynski et al. |
| 7,651,501 | B2 | | 1/2010 | Penenberg et al. |
| 2002/0133157 | A1 | * | 9/2002 | Sterett ................ A61B 17/8095 606/286 |
| 2004/0087944 | A1 | * | 5/2004 | Hazebrouck .......... A61F 2/4637 606/53 |
| 2004/0106927 | A1 | * | 6/2004 | Ruffner ................ A61B 17/025 606/90 |
| 2005/0222609 | A1 | | 10/2005 | Fankhauser et al. |
| 2007/0005145 | A1 | * | 1/2007 | Banks ................... A61F 2/3609 623/23.42 |
| 2007/0078464 | A1 | | 4/2007 | Jones et al. |
| 2007/0100347 | A1 | * | 5/2007 | Stad ..................... A61F 2/4611 606/90 |
| 2011/0040341 | A1 | | 2/2011 | Stad et al. |
| 2011/0218637 | A1 | * | 9/2011 | Termanini ................ A61F 2/32 623/22.15 |
| 2014/0142583 | A1 | | 5/2014 | Fortin et al. |

OTHER PUBLICATIONS

Written Opinion of the International Searching Authority for corresponding application PCT/US2016/042424 dated Oct. 4, 2016.
International Preliminary Report on Patentability for corresponding application PCT/US2016/042424 dated Jan. 30, 2018.

* cited by examiner

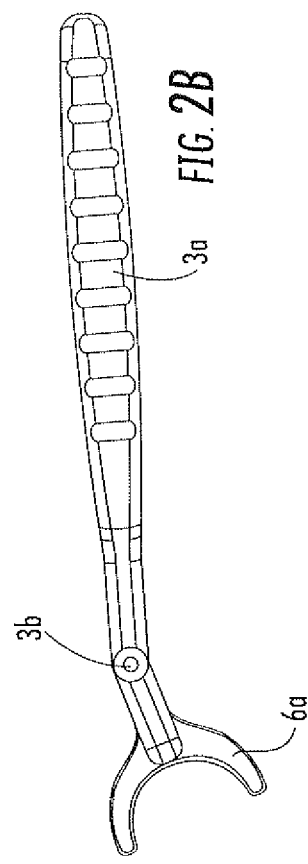
FIG. 2A
FIG. 2B
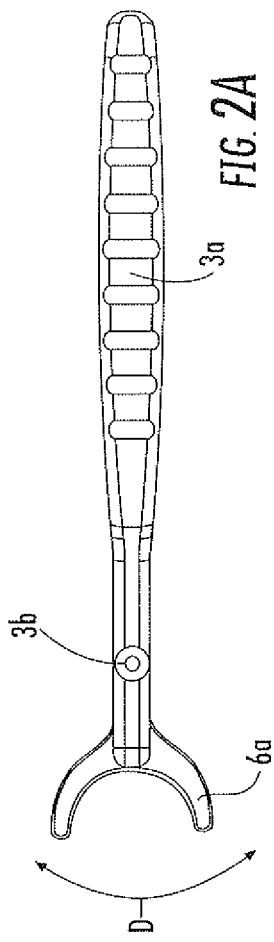
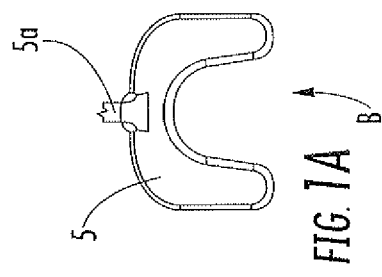
FIG. 1A
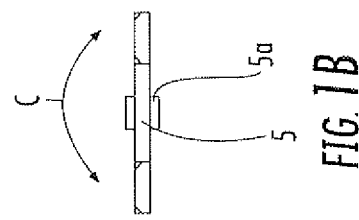
FIG. 1B

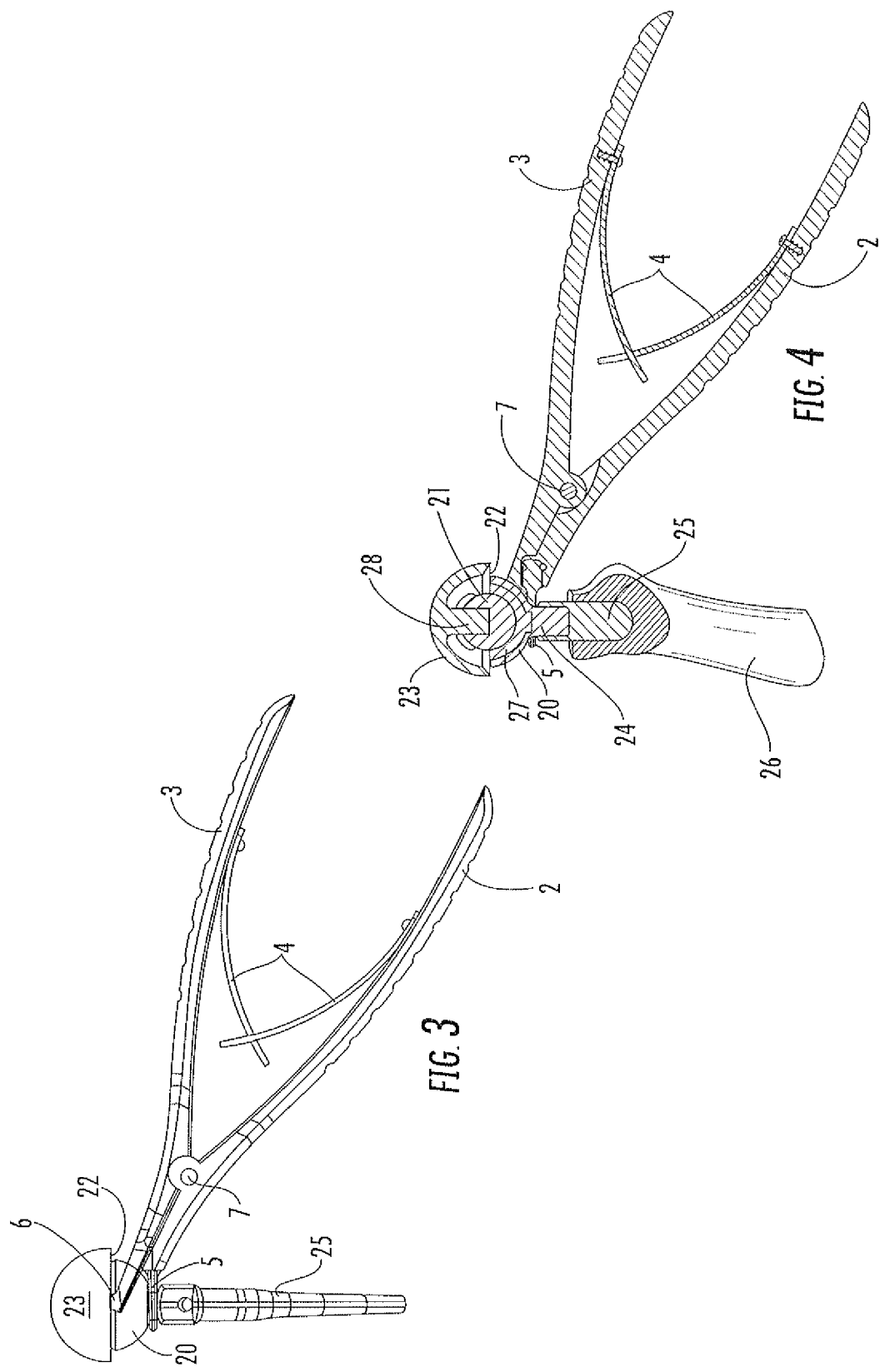

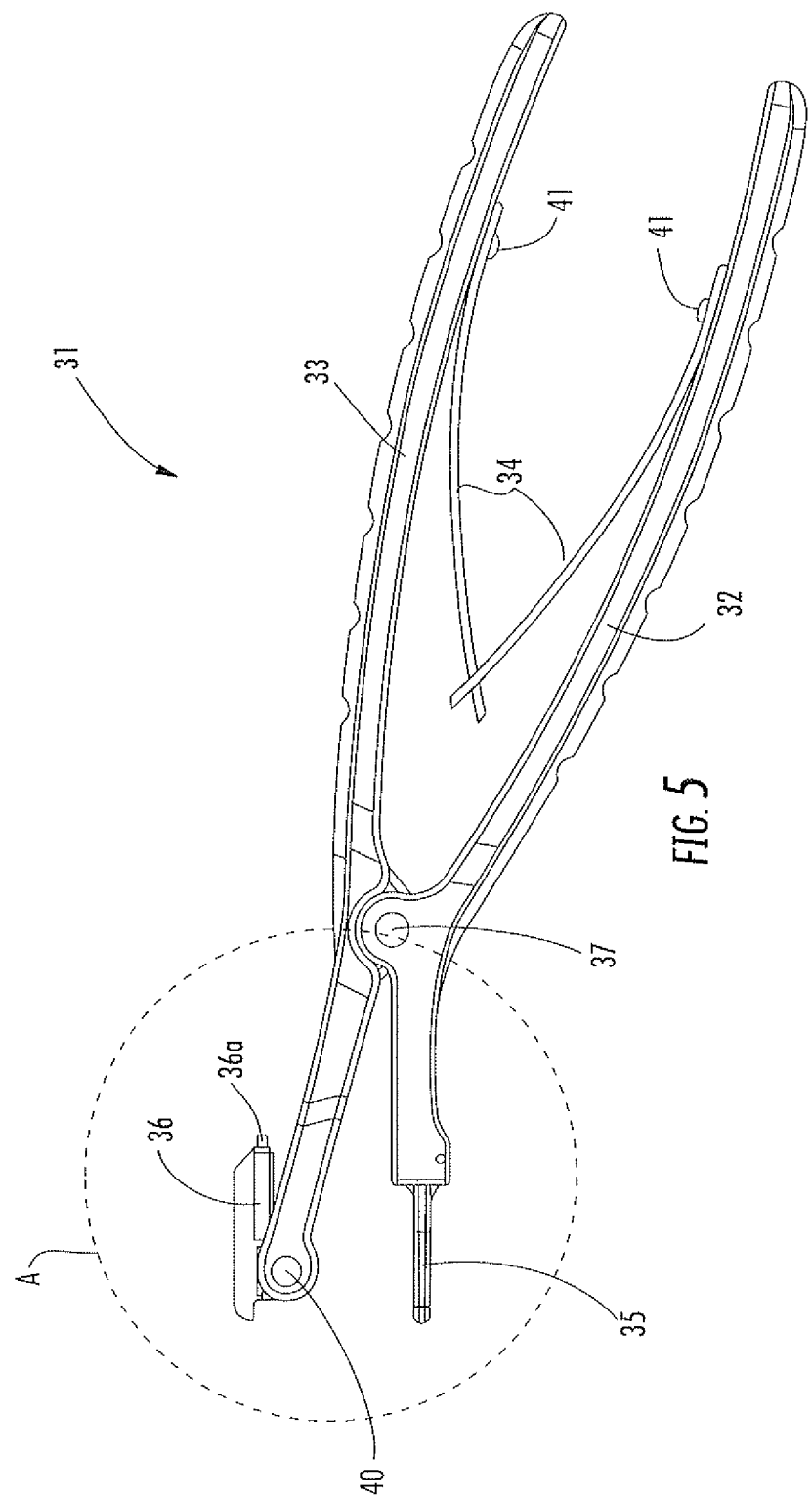

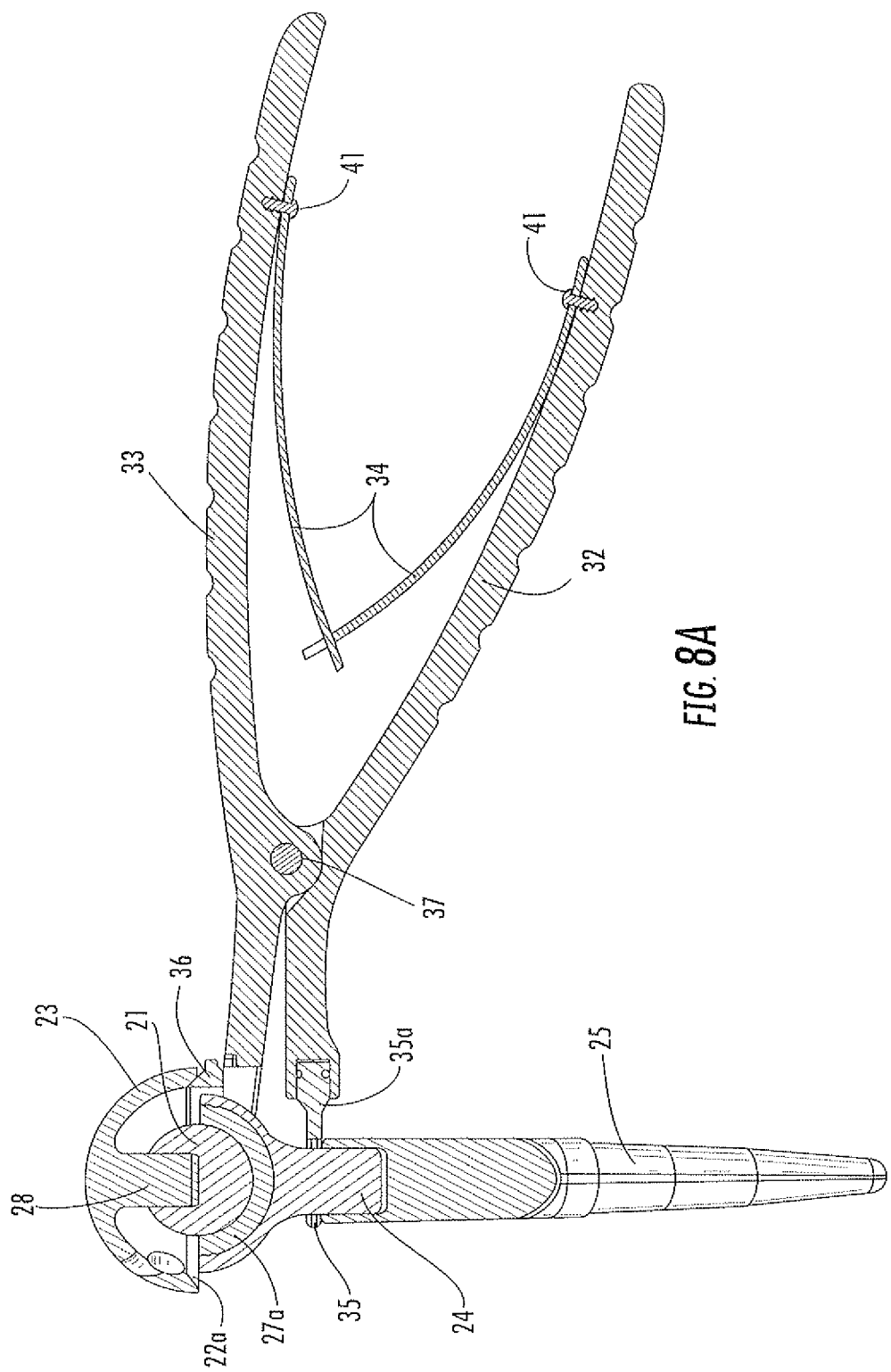

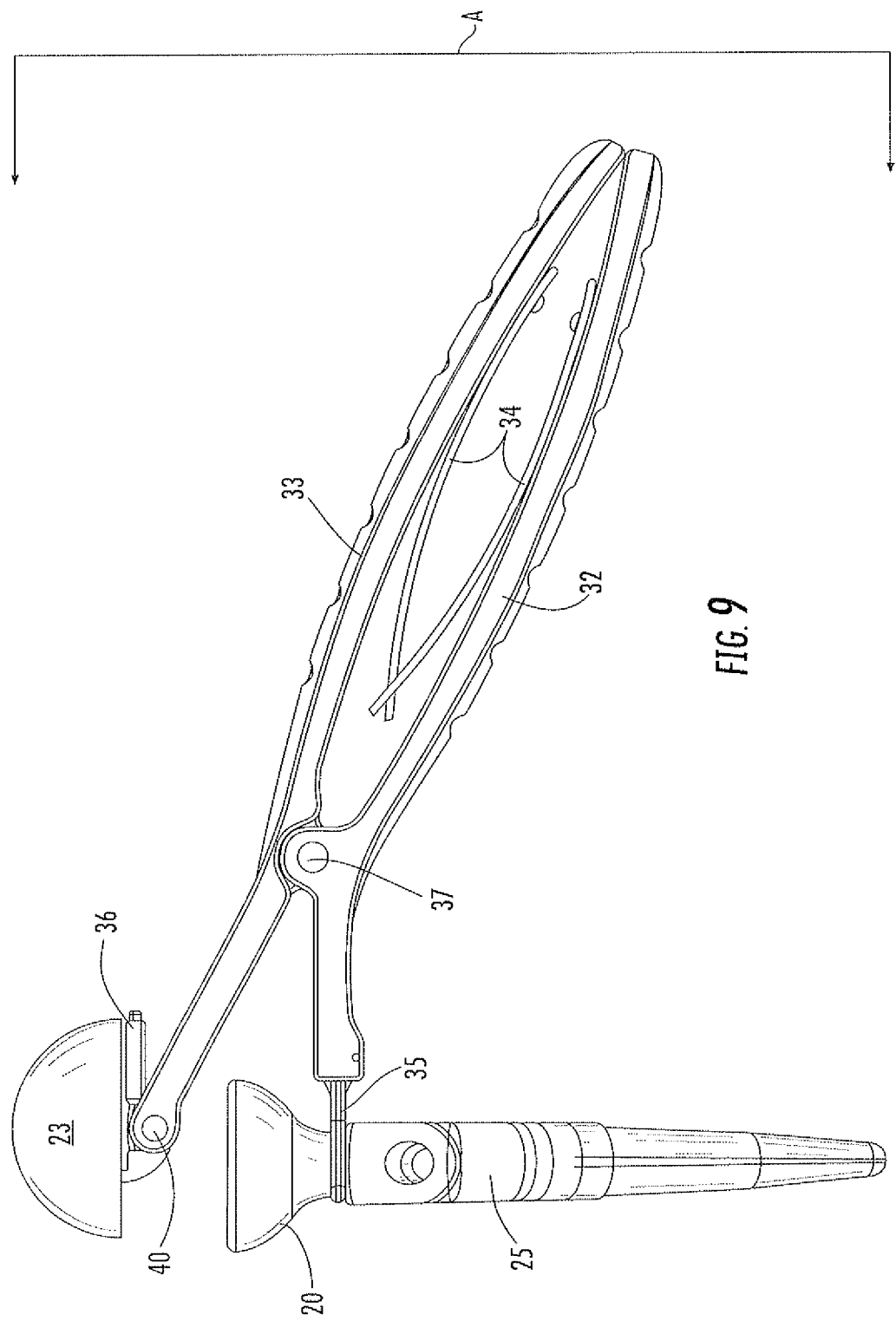

TOOL AND STATUS FOR SEPARATING A FEMORAL CUP FROM AN ACETABULAR BALL IN AN IMPLANTED HIP PROSTHESIS

This is an application filed under 35 USC 371 based on PCT/US2016/042424 filed 15.Jul.2016, which in turn claims priority to U.S. Ser. No. 62/197188 filed 27.Jul.2015. The present application claims the full priority benefit of these prior applications and herein incorporates by reference the full disclosures of these prior applications as if set forth herein.

BACKGROUND OF THE INVENTION

Field of the Invention

The present invention relates to surgical instruments used in connection with a hip prosthesis. More specifically, the invention has to do with surgical tools which are used to separate a femoral cup from an acetabular ball in an implanted hip replacement prosthesis.

The Related Art

A reverse hip prosthesis is described in U.S. Pat. Nos. 8,313,531 B2 and 8,540,779 B2. The prosthesis and a revision surgery method also are described in U.S. Pat. No. 8,992,627 B2. The disclosures of these three patents are incorporated herein in their entireties by reference.

SUMMARY OF THE INVENTION

As described in the patents referenced above, a femoral cup articulates on an acetabular ball when the prosthesis is implanted in a patient. The acetabular ball is affixed by means of a Morse taper to a stem which is affixed to and extends from the bottom of the concave surface of an acetabular cup. The surgical tools of the invention enable a surgeon to separate the femoral cup from the acetabular ball without pulling on the acetabular cup or the femoral implant and without disrupting any bone ingrowth. The surgical tool of the invention may be included as a component of a kit containing other surgical instruments and/or implant elements.

BRIEF DESCRIPTION OF THE DRAWINGS

FIG. 1A is a top elevation view of the femoral engagement component 5 of the first embodiment.

FIG. 1B is an end elevation view of FIG. 1A.

FIG. 2A is a bottom elevation view of an alternate embodiment of the second handle 3 of the first embodiment.

FIG. 2B is the same view as FIG. 2A following movement of the acetabular engagement component 6a.

FIG. 3 is a side elevation view of the tool of FIG. 2 positioned on a prosthesis just prior to separation of the femoral cup from the acetabular ball.

FIG. 4 is a section view of FIG. 3 with a partial section of a femur as an added element.

FIG. 5 is a side elevation view of a second embodiment of the tool of the invention wherein the handles have been squeezed toward one another.

FIG. 8A is a section view of FIG. 8.

FIG. 9 is a side elevation view of the second embodiment engaged with a femoral implant/cup and an acetabular cup after the femoral cup and acetabular cup have been separated from one another.

DESCRIPTION OF THE PREFERRED EMBODIMENTS

Figure 1:
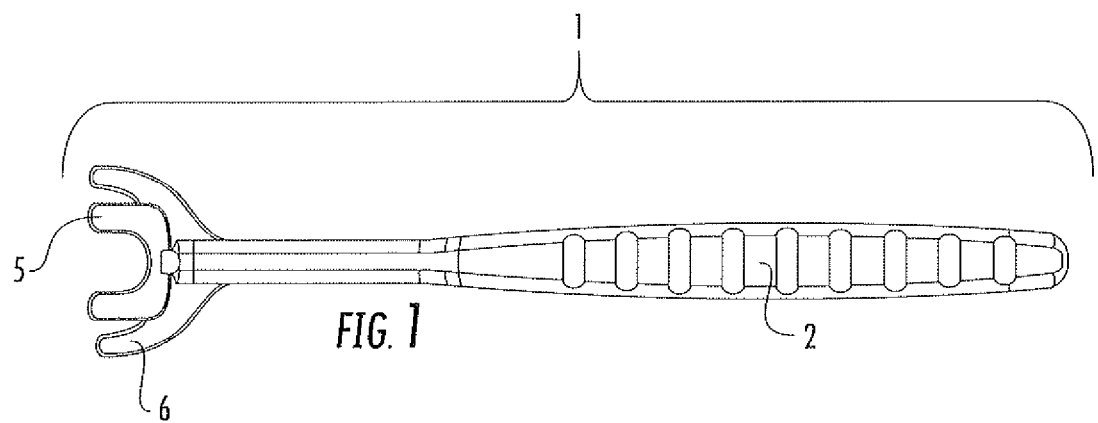
FIG. 1 is a top elevation view of a first embodiment of a surgical tool of the invention.
Figure 2:
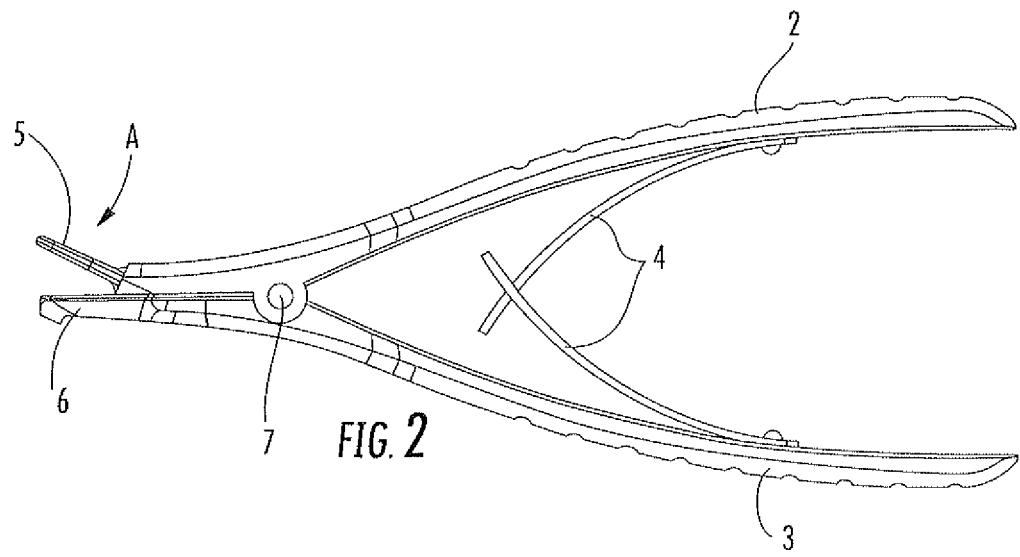
FIG. 2 is a side elevation view of the first embodiment of the surgical tool of the invention.

Referring to the first embodiment, the surgical tool 1 of the invention, also referred to herein as a surgical instrument, is illustrated in a top elevation view in FIG. 1 and a side elevation view in FIG. 2. The tool has a first handle 2 and a second handle 3. Springs 4 tend to bias the handles apart from one another as illustrated in FIG. 2. The distal end of the first handle 2 has a femoral engagement component 5 attached thereto and the distal end of the second handle 3 has an acetabular engagement component 6 attached thereto. Fulcrum pin 7 hinges the first handle 2 to the second handle 3 so that when the handles are squeezed toward one another the femoral engagement component 5 and the acetabular engagement component 6 are moved away from one another. The pin 7 thus provides a fulcrum between the first and second handles.

The femoral engagement component 5 illustrated in FIG. 1A is viewed from the direction of arrow A in FIG. 2. Femoral engagement component 5 may be rotatably connected to first handle 2 by means of axis pin 5a. Axis pin 5a allows a femoral engagement component 5 to rotate axially about the central axis of the first handle 2. In FIG. 1B, an end view of femoral engagement component 5 is illustrated as taken from the direction of arrow B in FIG. 1A. Arrow C in FIG. 1B illustrates the directions in which femoral engagement component 5 can be rotated.

FIGS. 2A and 2B illustrate a bottom elevation view of an alternate embodiment of the second handle which is designated as 3a. A hinge 3b is provided on handle 3a to allow lateral pivoting of a portion of the handle located between pin 7 (see FIG. 2) and acetabular engagement component 6a. Hinge 3b allows lateral movement in the directions of arrow D of FIG. 2A. FIG. 2B provides an example of a hinged handle 3a having an acetabular engagement component 6a at the distal end thereof.

In FIGS. 3 and 4 the surgical tool 1 is positioned on a prosthesis just prior to separation of the femoral cup 20 from the acetabular ball 21. The acetabular engagement component 6 is engaged with the circumferential edge 22 of acetabular cup 23 and the femoral engagement component 5 is engaged with the neck 24 of femoral cup 20, or the outer hemispherical surface of femoral cup 20, or both the neck 24 and the outer hemispherical surface of femoral cup 20. And the femoral engagement component 5 may also engage the top (i.e., the proximal end) of femoral implant 25 which is implanted in femur 26, shown in partial section. A liner 27 is illustrated in femoral cup 20. The acetabular ball 21 is affixed to stem 28 of the acetabular cup.

When handles 2 and 3 or 2 and 3a are squeezed toward one another, the femoral cup is separated from the acetabular ball.

The second embodiment of the surgical tool of the invention is very similar to the first embodiment except for the acetabular engagement element. This embodiment is illustrated in FIGS. 5-9A and it is designated as tool 31. A pivotable partial ring, referred to herein as acetabular engagement ring 36, is employed to engage the acetabular cup in the second embodiment as distinguished from acetabular engagement component 6 in the first embodiment. The term "acetabular engagement element" may be used herein to refer to both the acetabular engagement component 6 and the acetabular engagement ring 36.

Figure 5A:
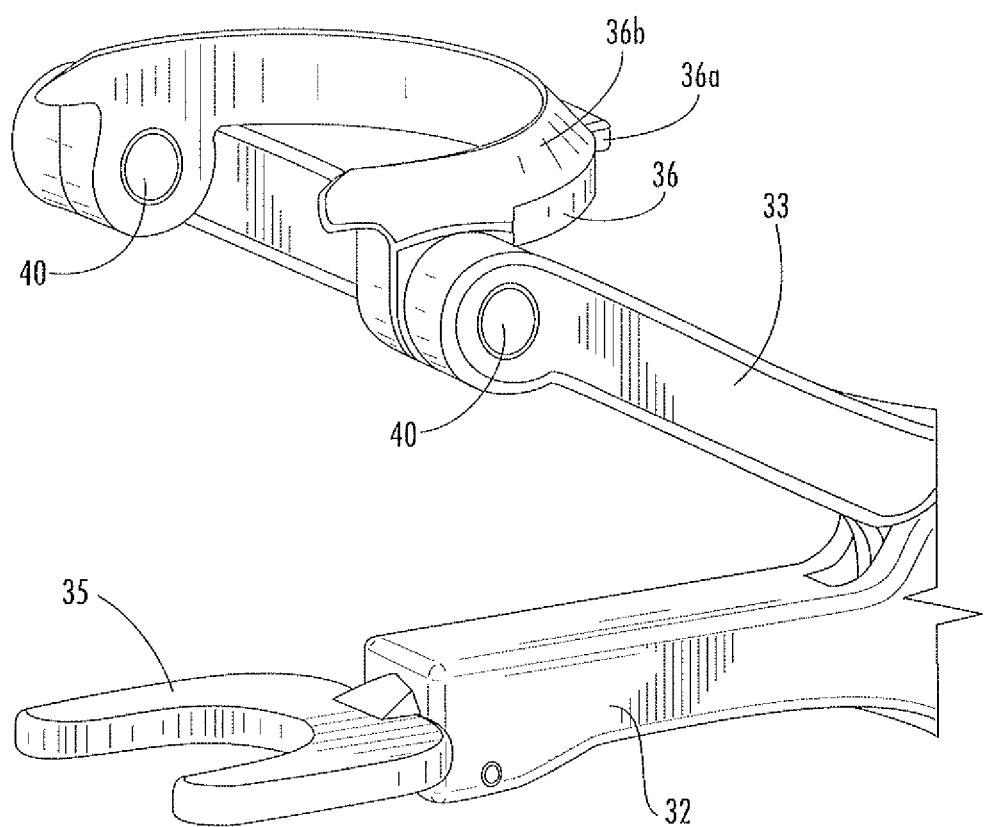
FIG. 5A is a perspective view of portion A of FIG. 5.
Figure 6:
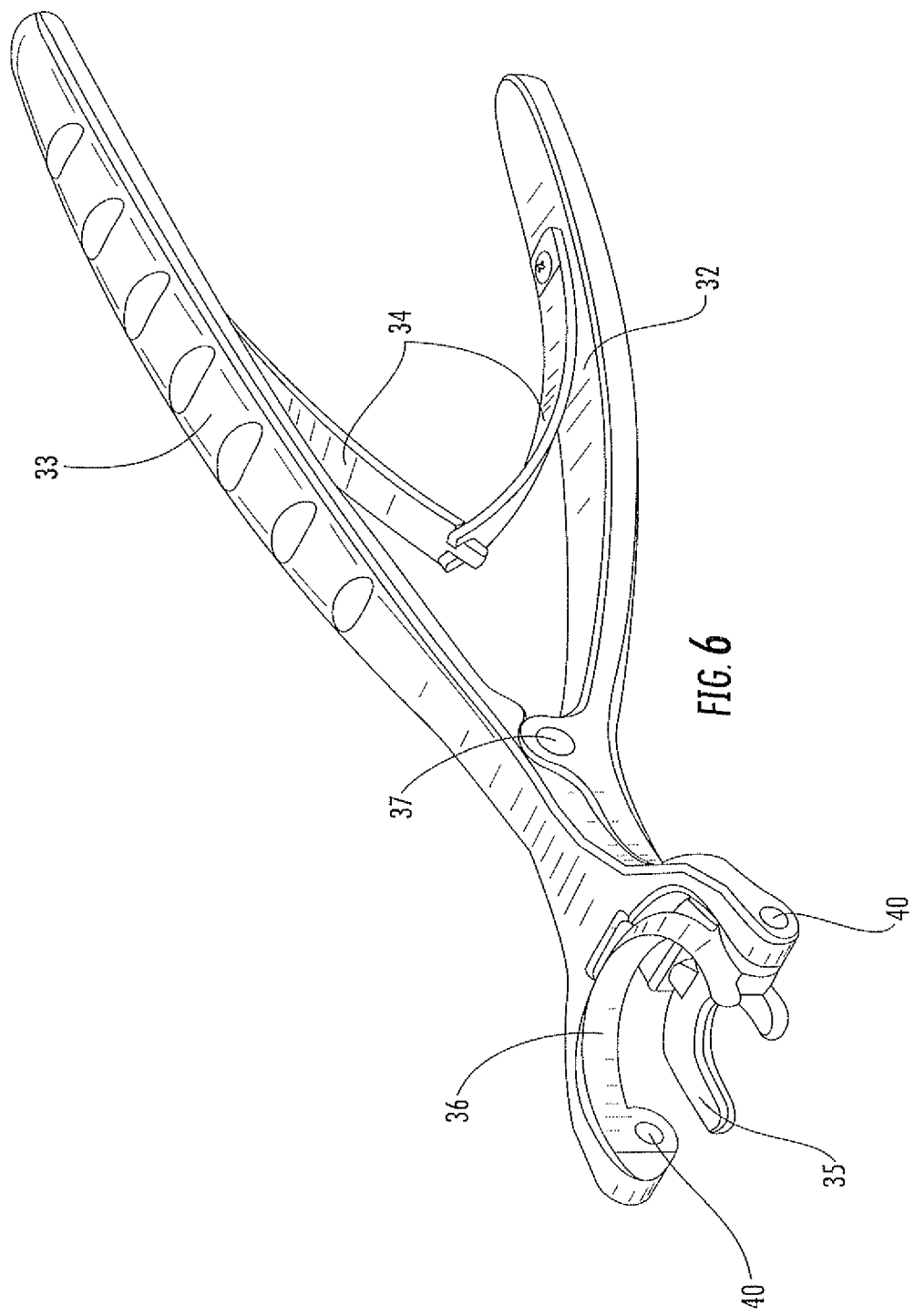
FIG. 6 is a perspective view of the second embodiment wherein the handles have not been squeezed toward one another.

FIG. 5 is a side elevation view of tool 31. The tool has a first handle 32 and a second handle 33. Springs 34, affixed to the handles with screws 41, tend to bias the handles apart from one another. And in FIG. 5, the handles have been squeezed toward one another to an intermediate position between fully open as shown in FIG. 6 and fully closed as shown in FIG. 9. The distal end of first handle 32 has a femoral engagement component 35 attached thereto. The distal end of second handle 33 has an acetabular engagement ring 36 pivotably attached thereto by means of ring pins 40. (See also FIG. 5A.) As can be seen from the drawings, ring 36 is pivotable about an axis which is perpendicular to the central axis of the distal portion of handle 33. Fulcrum pin 37 hinges the first handle 32 to the second handle 33 so that when the handles are squeezed toward one another the femoral engagement component 35 and the acetabular engagement ring 36 are moved away from one another. The pin 37 thus provides a fulcrum between the first and second handles.

As in the first embodiment, the femoral engagement component 35 of the second embodiment may be rotatably connected to first handle 32 by means of axis pin 35a. Axis pin 35a allows the femoral engagement component 35 to rotate axially about the central axis of the first handle 32 in the same manner as femoral engagement component 5 is allowed to rotate axially about the central axis of first handle 2 in the first embodiment. The alternate embodiment of second handle 3a which has a hinge 3b as described above (See FIG. 2B) can also be used with the second embodiment of the tool of the invention.

Figure 7:
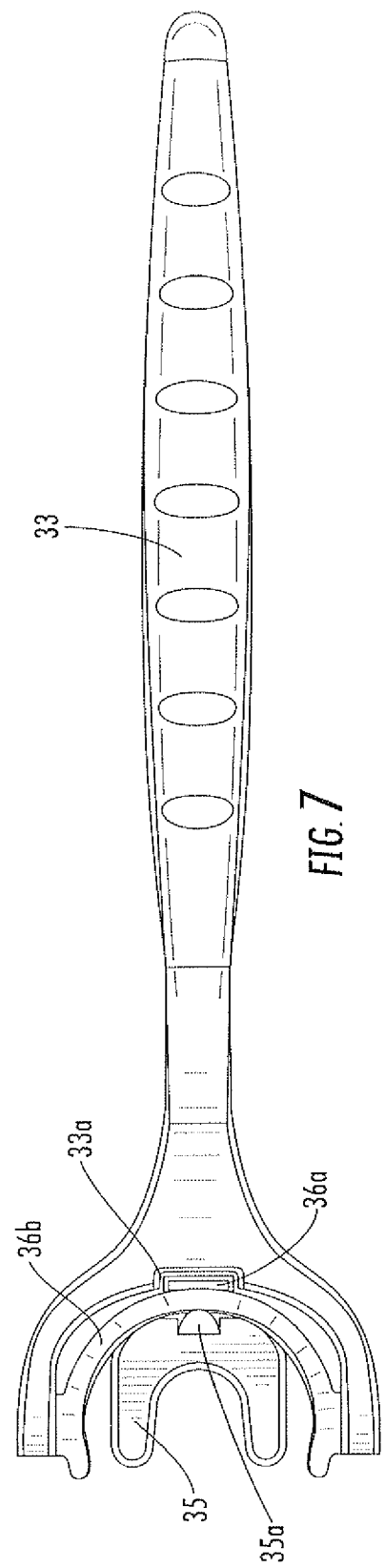
FIG. 7 is a top elevation view of FIG. 6.

Referring to FIGS. 5A, 7, 8A and 9A, acetabular engagement ring 36 has a beveled edge 36b which engages beveled edge 22a of acetabular cup 23. Ring 36 also has a tab 36a which is seated in indent 33a to prevent downward rotation of ring 36 below the horizontal central plane of the distal end of handle 33. Thus, as can be seen in FIGS. 6 and 7 wherein the handles are in the fully open position, tab 36a is seated in indent 33a and ring 36 is prevented from downward rotation in that position.

Figure 8:
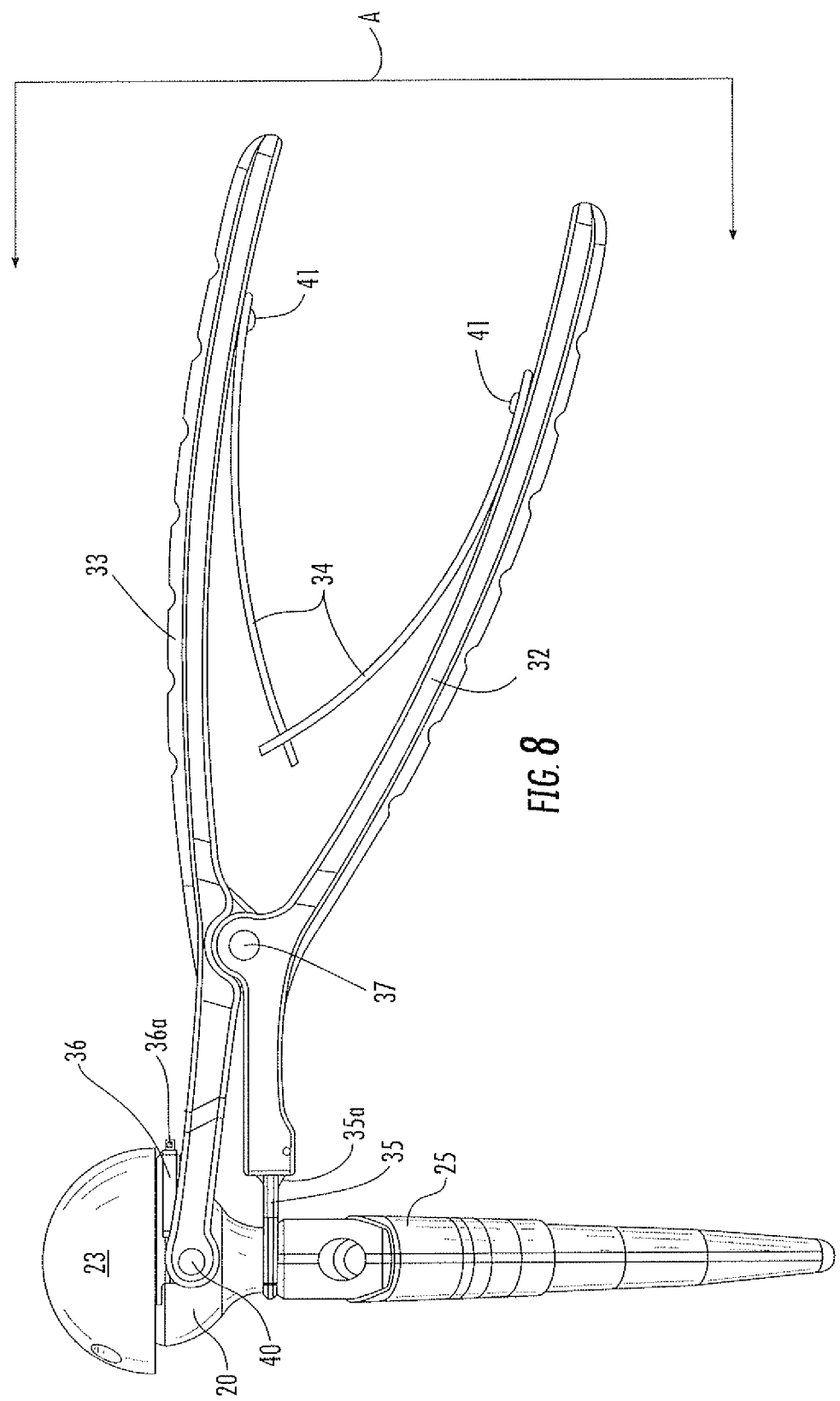
FIG. 8 is a side elevation view of the second embodiment engaged with a femoral implant/cup and an acetabular cup before the femoral cup and acetabular cup are separated from one another.

In FIGS. 8 and 8A the surgical tool 31 is positioned on a prosthesis just prior to separation of the femoral cup 20 from the acetabular ball 21. The beveled edge 36b of acetabular engagement ring 36 is engaged with the circumferential beveled edge 22a of acetabular cup 23 and the femoral engagement component 35 is engaged with the neck 24 of femoral cup 20 or the outer hemispherical surface of femoral cup 20, or both the neck 24 and the outer hemispherical surface of femoral cup 20. A femoral implant 25 is also illustrated and the femoral engagement component 35 may also engage the top (i.e., the proximal end) of implant 25. A liner 27 is illustrated in femoral cup 20. The acetabular ball 21 is affixed to stem 28 of the acetabular cup.

Figure 9A:
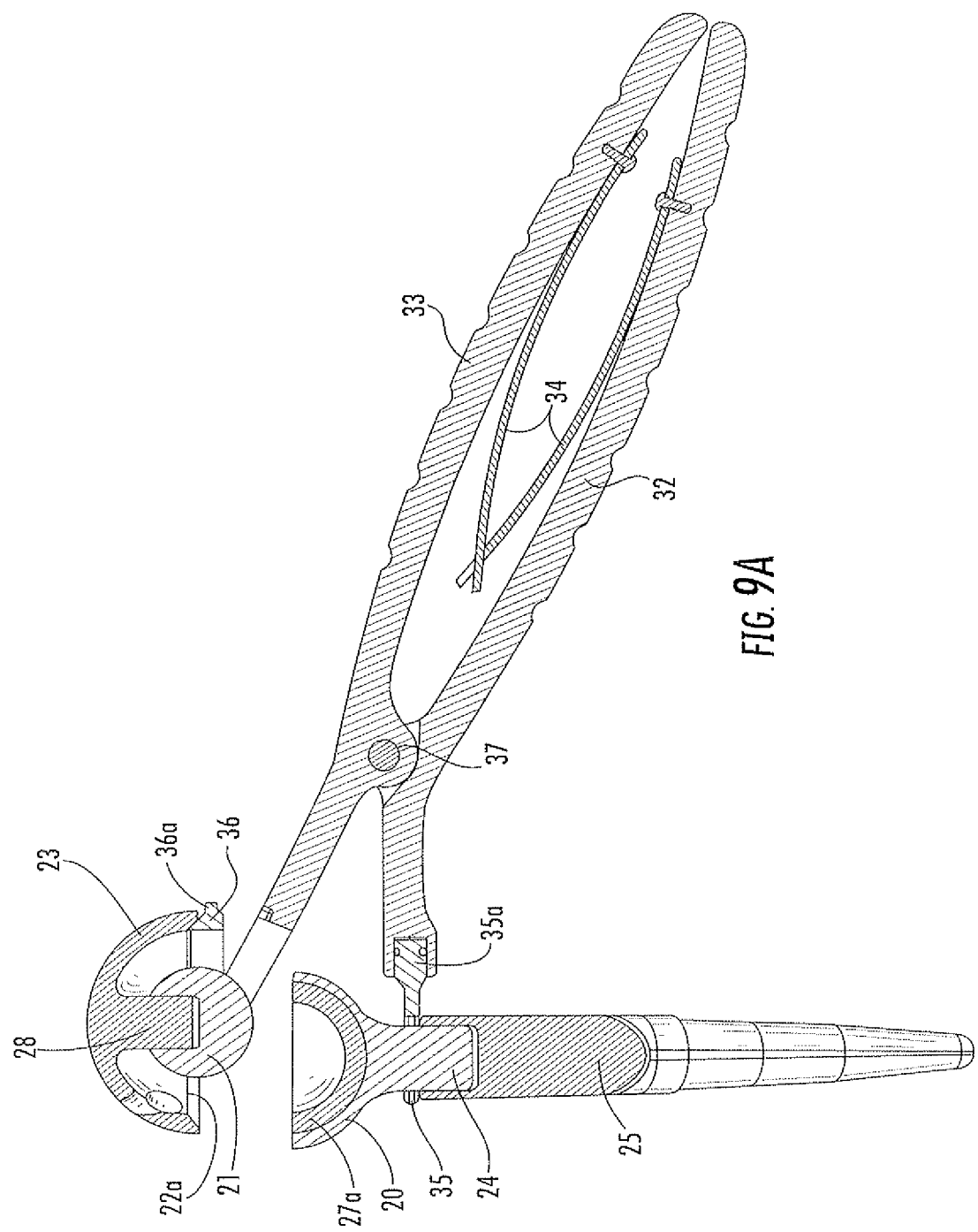
FIG. 9A is a section view of FIG. 9.

When handles 32 and 33 are squeezed toward one another the femoral cup is separated from the acetabular ball as shown in FIGS. 9 and 9a.

In the surgical method of the invention, femoral engagement component 5 or 35 is engaged with the neck of the femoral cup, or an outer hemispherical surface of the femoral cup or both the neck and the outer hemispherical surface of the femoral cup and/or the upper surface (i.e. the proximal end) of a femoral implant. Simultaneously, the acetabular engagement component 6 is engaged with the circumferential edge 22 of the acetabular cup 23, or the circumferential beveled edge 36b of femoral engagement ring 36 is engaged with the circumferential beveled edge 22a of acetabular cup 23, and then the first and second handles are squeezed toward one another thereby causing the femoral cup and the acetabular ball to be separated from one another.

The invention claimed is:

1. A surgical tool comprising:
   a first handle and a second handle connected by a single fulcrum pin in a hinged relationship, the first and second handles being urged apart by a spring, each handle having a proximal end and a distal end;
   the first handle having a generally flat, generally U-shaped femoral engagement component at the distal end thereof;
   the second handle having a generally flat, generally U-shaped acetabular engagement component at the distal end thereof;
   the single fulcrum pin being disposed between the distal and proximal ends of each handle, whereby movement of the proximal ends towards one another causes the distal ends to move away from one another;
   the femoral engagement component which is axially rotatable with respect to the first handle about an axis non-parallel to an axis of handle rotation about the single fulcrum pin, and is sized to engage a neck of a femoral cup, an outer hemispherical surface of a femoral cup, or both a neck and an outer hemispherical surface of a femoral cup, or a top end of a femoral implant having mounted thereon a femoral cup, and,
   the acetabular engagement component is sized to engage only a part of a circumferential edge of an acetabular cup.

2. The surgical tool of claim 1 wherein the femoral engagement component is connected by means of an axis pin to the first handle, the first handle having a central axis and the femoral engagement component is axially rotatable about the central axis.

3. The surgical tool of claim 1 further comprising a hinge disposed between the fulcrum pin and the acetabular engagement component, the hinge being arranged to allow lateral movement of the acetabular engagement component relative to the second handle.

4. A kit containing at least one other surgical instrument and/or an implant element, and the surgical tool of claim 1.

5. A method of using the surgical tool of claim 1 comprising:
   engaging the surgical tool such that the acetabular engagement component is engaged with a circumferential edge of an acetabular cup, and concurrently engaging the femoral engagement component with a neck of a femoral cup, an outer hemispherical surface of a femoral cup, or a neck and an outer hemispherical surface of a femoral cup, or a top end of a femoral implant having mounted thereon a femoral cup;
   squeezing the first and second handles towards one another thereby causing the acetabular cup to move in a direction away from the neck of the femoral cup, or the outer hemispherical surface of the femoral cup, or the top end of the femoral implant having mounted thereon the femoral cup.

6. The method of claim 5, wherein the femoral cup is separable from the acetabular ball without pulling on the acetabular cup and without pulling on the femoral implant.

7. The method of claim 6, wherein the femoral cup is separable from the acetabular ball without pulling on the acetabular cup and without pulling on the femoral implant, and without disrupting any bone ingrowth when the femoral implant and the acetabular cup are implanted in bone.

8. The method of claim 5, wherein a transverse distance between legs of the U-shaped acetabular engagement component is greater than a transverse distance between legs of the U-shaped femoral engagement component.

9. The surgical tool of claim 1 wherein two legs of the U-shaped acetabular engagement component come into contact with the circumferential edge of the acetabular cup.

10. The surgical tool of claim 9, wherein each end of the two legs are lobe shaped.

11. The surgical tool of claim 1 wherein a transverse distance between legs of the U-shaped acetabular engagement component is greater than a transverse distance between legs of the U-shaped femoral engagement component.

12. The surgical tool of claim 1, wherein the U-shaped femoral engagement component is angled with respect to the U-shaped acetabular engagement component.

13. The surgical tool of claim 1, wherein the femoral engagement component rotates in a plane that is generally perpendicular to a plane of handle rotation about the single fulcrum pin.

* * * * *